(12) United States Patent
Johnson et al.

(10) Patent No.: US 7,559,928 B2
(45) Date of Patent: Jul. 14, 2009

(54) APPARATUS AND METHOD FOR MINIMALLY INVASIVE TOTAL JOINT REPLACEMENT

(75) Inventors: Wesley D. Johnson, Eden Prairie, MN (US); Gerard A. Engh, Alexandria, VA (US); Mike Travanty, Minneapolis, MN (US)

(73) Assignee: Alexandria Research Technologies, LLC, Plymouth, MN (US)

( * ) Notice: Subject to any disclaimer, the term of this patent is extended or adjusted under 35 U.S.C. 154(b) by 490 days.

(21) Appl. No.: 11/535,916

(22) Filed: Sep. 27, 2006

(65) Prior Publication Data

US 2007/0276394 A1  Nov. 29, 2007

Related U.S. Application Data

(60) Continuation-in-part of application No. 10/429,435, filed on May 3, 2003, which is a division of application No. 10/075,829, filed on Feb. 12, 2002, now Pat. No. 6,723,102.

(60) Provisional application No. 60/721,450, filed on Sep. 28, 2005.

(51) Int. Cl.
*A61B 17/00* (2006.01)

(52) U.S. Cl. .......................... 606/81; 606/39

(58) Field of Classification Search .............. 606/81, 606/79, 80, 82, 84, 85, 87, 88, 86 R, 39; 623/22.4, 623/23.11, 20.21, 22.11
See application file for complete search history.

(56) References Cited

U.S. PATENT DOCUMENTS

| 4,306,550 | A | | 12/1981 | Forte | |
|---|---|---|---|---|---|
| 5,057,112 | A | * | 10/1991 | Sherman et al. | 606/79 |
| 5,176,683 | A | * | 1/1993 | Kimsey et al. | 606/86 R |
| 5,919,195 | A | * | 7/1999 | Wilson et al. | 606/80 |
| 6,953,480 | B2 | * | 10/2005 | Mears et al. | 623/22.11 |
| 7,105,028 | B2 | * | 9/2006 | Murphy | 623/22.4 |
| 2003/0236523 | A1 | | 12/2003 | Johnson et al. | |
| 2004/0172036 | A1 | | 9/2004 | Dye | |

* cited by examiner

*Primary Examiner*—Pedro Philogene
(74) *Attorney, Agent, or Firm*—Barbara A. Wrigley; Oppenheimer, Wolff & Donnelly LLP

(57) ABSTRACT

A method and apparatus for minimally invasive total joint replacement is disclosed. The method involves sculpting the articular surface of a second bone that normally articulates with a first bone by attaching or supporting a bone sculpting tool directly or indirectly to the first bone with the tool in sculpting engagement with the articular surface of the second bone, and then sculpting the articular surface of the second bone with the joint reduced. The reamer system includes a reamer drive, a grater, a handle and a femoral broach.

29 Claims, 12 Drawing Sheets

APPARATUS AND METHOD FOR MINIMALLY INVASIVE TOTAL JOINT REPLACEMENT

CROSS REFERENCE TO RELATED APPLICATIONS

This application is a continuation-in-part and claims the benefit of U.S. provisional patent application Ser. No. 60/721,450 filed Sep. 28, 2005, which is a continuation-in-part of U.S. patent application Ser. No. 10/429,435 filed May 5, 2003, which is a divisional of U.S. patent application Ser. No. 10/075,829 filed Feb. 12, 2002 now U.S. Pat. No. 6,723,102, the entireties of which are hereby incorporated by reference.

BACKGROUND OF THE INVENTION

A joint generally consists of two relatively rigid bony structures that maintain a relationship with each other. Soft tissue structures spanning the bony structures hold the bony structures together and aid in defining the motion of one bony structure relative to the other. Soft tissue such as ligaments, tendons, menisci, and capsule provide support to the bony structures. A smooth and resilient surface consisting of articular cartilage covers the bony structures. The articular surfaces of the bony structures work in concert with the soft tissue structures to form a mechanism that defines the envelope of motion between the structures. When fully articulated, the motion defines a total envelope of motion between the bony structures. Within a typical envelope of motion, the bony structures move in a predetermined pattern with respect to one another. In the example of the hip joint, the joint is a ball in socket joint that is inherently stable. The capsule and ligaments spanning the hip joint provide stability while the muscles provide motion.

The articular surfaces of the bony structures may become damaged by a variety of diseases, accidents, and other causes. A common disorder of joints is degenerative arthritis. Degenerative arthritis causes progressive pain, swelling, and stiffness of the joints. As the arthritis progresses the joint surfaces wear away, resulting in contractures of the surrounding soft tissues that provide stability to the joint. Moreover, progression of the disease process increases pain and reduces mobility.

Treatment of the afflicted articular bone surfaces depends, among other things, upon the severity of the damage to the articular surface and the age and general physical robustness of the patient. Commonly, for advanced arthritis, joint replacement surgery is necessary wherein the articulating elements of the joint are replaced with artificial elements commonly consisting of a part made of metal articulating with a part made of ultra high molecular weight polyethylene (UHMWPE).

A relatively young patient with moderate to severe degeneration of the hip joint is often treated with drug therapies. While drug therapies may temporarily provide relief of pain, progression of the disease, with resulting deformity and reduced function, ultimately necessitates surgery. Alternative treatments such as non-steroidal anti-inflammatory drugs and cortisone injections similarly provide only temporary relief of symptoms. Accordingly, there exists a need for a source of permanent relief of symptoms associated with moderate to severe degeneration of the hip joint.

In severe situations, surgery may be indicated in which the articular surface of one or more of the bones related to the joint is partially or entirely replaced with an artificial surface, as, for example, when the acetabular socket and femoral head are replaced with a prosthetic device including an UHMWPE bearing to resurface the acetabulum and a polished metal or ceramic femoral head mounted to a stem extending into the medullary canal of the proximal femur to replace the femoral head. Joint replacement surgery has become a proven and efficacious method of alleviating pain and restoring function of the joint.

Current methods of preparing the rigid elements of a joint to receive components as in joint replacement surgery involve extensive surgical exposure. The exposure must be sufficient to permit the introduction of drills, reamers, broaches and other instruments for cutting or removing cartilage and bone that subsequently is replaced with artificial surfaces. For total hip replacement, the acetabular articular surface and subchondral bone is removed by hemispherical graters, the femoral head is resected with an oscillating saw, and the proximal medullary canal is shaped with broaches. A difficulty with total hip replacement is that the invasiveness of the procedure causes significant intraoperative blood loss and extensive rehabilitation because muscles and tendons must be released from the proximal femur to mobilize the femur and gain exposure of and access to the acetabular fossa.

Conventional total hip arthroplasty is indicated for painful arthritis of the hip joint. The procedure involves exposing the hip joint through a large incision to provide the surgeon full visualization of the hip joint and the acetabular region and to provide access for surgical power instruments. In order to appropriately prepare the bony structures of the hip joint, the major muscles spanning the joint are commonly disrupted to gain adequate exposure of the joint. Steps of the procedure include removing the femoral head followed by reaming and broaching the proximal femoral canal to prepare a bony surface to support a hip stem. The stem is implanted and may be cemented in place, or press fit for bony ingrowth. The acetabulum is typically prepared using sequentially sized graters to remove cartilage down to bleeding bone. Once the acetabulum is prepared, an acetabular component is implanted, either by cementing in place or press fitting for bony ingrowth. Extensive surgical exposure is necessary to accommodate the bulk and geometry of the components as well as the instruments for bone preparation. The surgical exposure, which may be between six and twelve inches in length, may result in extensive trauma to the soft tissues surrounding the hip joint along with the release of muscles that insert into the proximal femur. The surgical exposure increases bleeding, pain, and muscle inhibition; all of which contribute to a longer hospitalization and rehabilitation before the patient can be safely discharged to home or to an intermediate care facility.

The prepared bony surfaces are technically referred to as the acetabular fossa, femoral canal and metaphyseal region of the femur. Prior to placing the final implants into the prepared spaces, a femoral trial, which may be the broach in some systems, is placed in the proximal femur along with a trial femoral head and neck, and an acetabular trial is placed into the acetabulum to facilitate trial range of motion and evaluation of hip stability prior to placement of the final total hip implants.

Devices for minimally invasive hip surgery that prepare the acetabulum to receive final total hip implants are known. Hemispherical graters driven with straight drive handles connected to a surgical drill have been used. However, soft tissue structures limited proper orientation of these devices leading to the development of curved drive handles used to avoid soft tissue interference. The resulting reamer device, while partially avoiding soft tissue structures, still required the surgeon to force the handle against soft tissue structures to gain proper orientation of the grater. In addition, such devices still required retraction of the proximal femur to provide access for the handle and grater to the acetabulum. Extensive distraction force is needed to displace the femur resulting in trauma to soft tissue structures because of the magnitude and duration of the force imparted.

An acetabular grater that rotates about an axis transverse to the drive handle longitudinal axis is known for preparation of the acetabulum to receive an implant. The reamer device includes a grater and a drive handle. The drive handle has a pivotable head to which the grater attaches. The grater is rotated about the pivotable head to reduce the grater profile for a surgical incision. Once in the acetabulum, the grater rotates normal to the drive handle during operation. The grater includes cutouts in the hemispherical shell to allow rotation over the drive handle. As with the straight and curved drive handles described above, a pivotable head drive handle interferes with soft tissue structures while preparing the acetabulum and requires distraction of the femur to allow access to the acetabulum.

Based on the foregoing, there exists a need for surgical methods and apparatuses that may be employed to gain surgical access to articulating joint surfaces, to appropriately prepare the bony structures, to provide artificial, e.g., metal or plastic, articular bearing surfaces, and to close the surgical site, all without substantial damage or trauma to associated muscles, ligaments or tendons. There also exists a need for a system and method that enables articulating surfaces of the joints to be appropriately sculpted using minimally invasive apparatuses and procedures. There exists another need for a surgical navigation system to guide the preparation of articular surfaces and to position the acetabular implant.

SUMMARY OF THE INVENTION

The present invention provides a system and method for total joint replacement that involves minimally invasive surgical procedures. The instruments disclosed accomplish accurate bone preparation through a limited surgical exposure.

Thus, in one embodiment, the present invention provides a method of appropriately sculpting the articular surface of a second bone that normally articulates with a first bone. The method involves attaching a bone sculpting tool directly or indirectly to the first bone with the tool in bone sculpting engagement with the articular surface of the second bone, and then sculpting the articular surface of the second bone with the joint reduced. Sculpting of the second bone is done by moving one bone with respect to the other. Alternatively, sculpting of the second bone is done by orienting the first bone appropriately relative to the second bone and advancing the sculpting tool into or onto the second bone. In another embodiment, sculpting of the second bone is done by orienting the sculpting tool relative to the second bone while supporting the sculpting tool on the first bone and advancing the sculpting tool into or onto the second bone. Optionally, the bone sculpting tool may be attached to a mount that is attached directly or indirectly to the first bone. Force to advance the sculpting tool into or onto the second bone is provided by a distraction device integral to the sculpting tool. Optionally, the distraction device may be independent of the sculpting tool. Alternatively, the force to advance the sculpting tool into or onto the second bone may be provided by the weight of the extremity or by the surgeon applying force to the extremity.

In a further embodiment, the invention provides a method of appropriately preparing the articular surface of a second bone that normally articulates with a first bone and implanting a prosthetic device. The method involves attaching a bone sculpting tool directly or indirectly to the first bone with the tool in bone sculpting engagement with the articular surface of the second bone, and then sculpting the articular surface by articulating one of the bones with respect to the other while bone preparation is performed. Optionally, the sculpting tool may be supported by the first bone with the tool in bone sculpting engagement with the articular surface of the second bone, and then sculpting the articular surface by articulating the tool with respect to the first bone. Alternatively, the sculpting tool may be supported by the first bone with the tool in bone sculpting engagement with the articular surface of the second bone, and then sculpting the articular surface by advancing the tool into or onto the second bone while maintaining the relative orientation of the tool to the second bone. The bone sculpting tool may be supported by an implant, a trial, a reamer or a broach placed in or on a bone. Alternatively, the bone sculpting tool may be attached to or integral with an implant, a trial, a reamer or a broach placed in or on a bone. Optionally, the bone sculpting tool may be attached to a bone mount that is directly or indirectly attached to or integral with an implant, a trial, a reamer or a broach placed in or on a bone.

Specifically, for example, the invention may be used for replacing the surfaces of a femur and acetabulum through a minimal incision and with minimal disruption of musculotendinous structures about the hip. A typical incision for a minimally invasive total hip procedure is between two and four inches in length. It is noted that there may be some variation in incision length due to patient physiology, surgeon preferences, and/or other factors; the stated range is illustrative, not limiting. In addition to a small incision, care is taken to approach the joint capsule by separating tissues between muscle groups, rather than sectioning specific muscles. The invention includes, in various embodiments, a reamer system. The reamer system in accordance with the present invention is either a modular or non-modular construct that, for hip applications, comprises a femoral attachment component which is typically a femoral trial, a reamer drive (either integral or separate), a handle, and a hemispherical grater or similar device for removing cartilage and bone from the acetabular fossa. The reamer system is powered by a power source such as a standard surgical drill. Optionally, the reamer system may be powered by an integral power source such as an electric, pneumatic or hydraulic motor, a solenoid, an electromechanical drive or other suitable power source. The reamer system is designed or structured to be placed into the joint cavity via one or more small incisions while leaving most, if not all, muscles intact. Surgical navigation may be used to aid in positioning the reamer system and in monitoring progression of acetabular preparation by attaching a navigational tracker to the pelvis and a second navigational tracker to the reamer drive. Optionally, the second navigational tracker may be attached to the handle. Once the femur and acetabulum have been prepared, the implants are placed without further muscle release or surgical trauma.

In a minimally invasive procedure, the hip is accessed through an incision adequate to expose the trochanteric fossa and allow resection of the femoral neck and removal of the femoral head and neck segment. The femoral canal is accessed through the trochanteric fossa and trochanteric region. Reamers, rasps and other devices as are known to those skilled in the art are used to prepare the proximal femur to receive a femoral implant by a sequence of reaming and broaching steps. Once prepared the intramedullary canal and retained area of the femoral neck and trochanteric region support a femoral broach which in turn supports the reamer system to prepare the acetabulum.

DETAILED DESCRIPTION OF THE INVENTION

Figure 1:
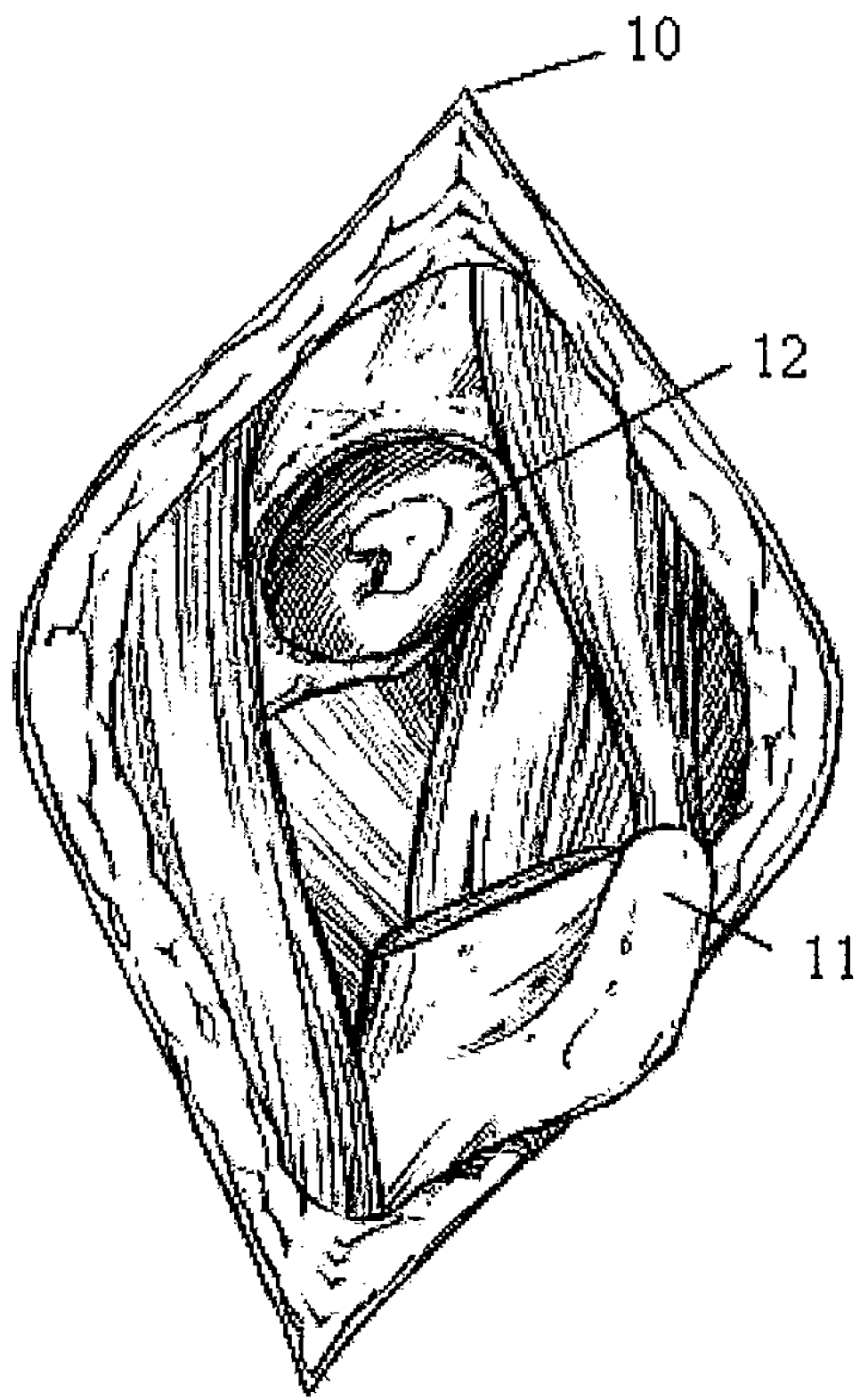
FIG. 1 is an illustration of hip anatomy and conventional exposure for total hip replacement.

FIG. 1 illustrates the general anatomy of a hip joint and a typical surgical approach 10 to the hip joint to expose a proximal femur 11 and an acetabulum 12. Four surgical approaches to the hip joint for total hip replacement are known. These approaches include posterior approaches without trochanteric osteotomy, trans-trochanteric approaches, anterior approaches without trochanteric osteotomy, and Smith-Peterson approaches. A direct lateral approach is also known for total hip arthroplasty. The most common surgical approach to the hip is posterior, and the musculature disrupted may include the short internal and external rotators, tensor fascia femoris, quadratus femoris, piriformis, and on occasion part of the gluteus medius and minimus, and the gluteus maximus.

In conventional total hip replacement surgery the hip joint is exposed through a large incision to provide the surgeon full visualization of the hip joint and the acetabular region, and to provide access for surgical power instruments. The femoral head is removed and the femoral canal is reamed and broached to prepare a bony surface to support a hip stem. The stem may be cemented in place, or press fit for bony ingrowth. The acetabulum is prepared, most typically using a grater attached to a surgical hand drill to remove cartilage down to bleeding bone. The skin incision for surgical exposure as shown in FIG. 1 generally ranges between eight and twelve inches in length with partial or complete release of hip abductors and external rotators resulting in extensive trauma to the soft tissues surrounding the hip joint.

Figure 2:
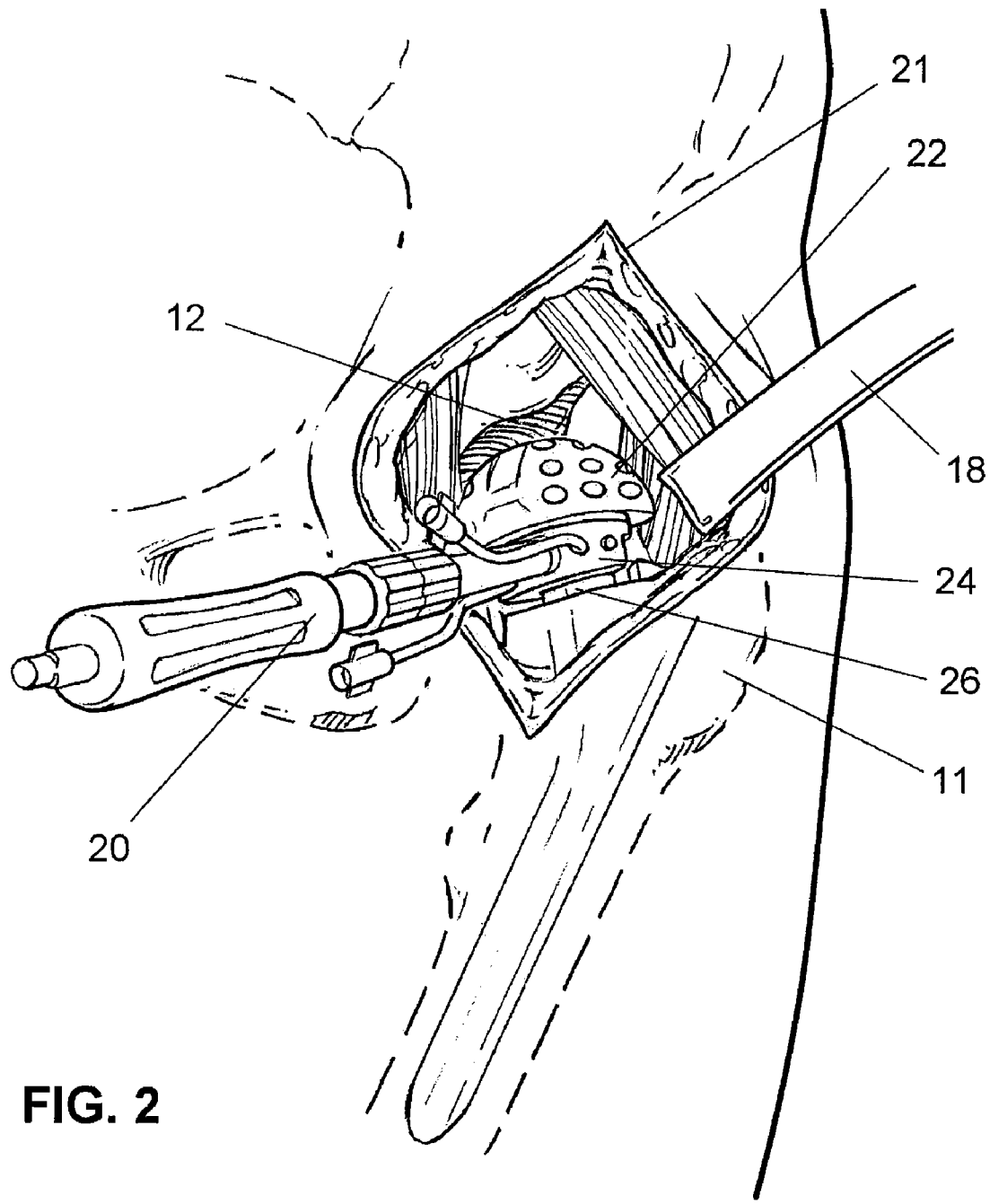
FIG. 2 is an illustration of exposure for minimally invasive total hip replacement with a reamer system.

In minimally invasive total hip surgery, an incision 21 is typically two to four inches in length as shown in FIG. 2. While a two to four inch surgical incision is typical for less or minimally invasive hip surgery, there may be some variation due to patient physiology, surgeon preferences, or other factors. The surgical approach involves separating the gluteus maximus muscle through blunt dissection to gain access to the hip joint capsule and the trochanteric fossa. Muscle disruption is usually limited to release of the piriformis tendon at the trochanteric fossa. Those skilled in the art can appreciate that variations to the surgical approaches described herein can be varied according to individual patients, preference of the surgeon and the like.

Figure 3A:
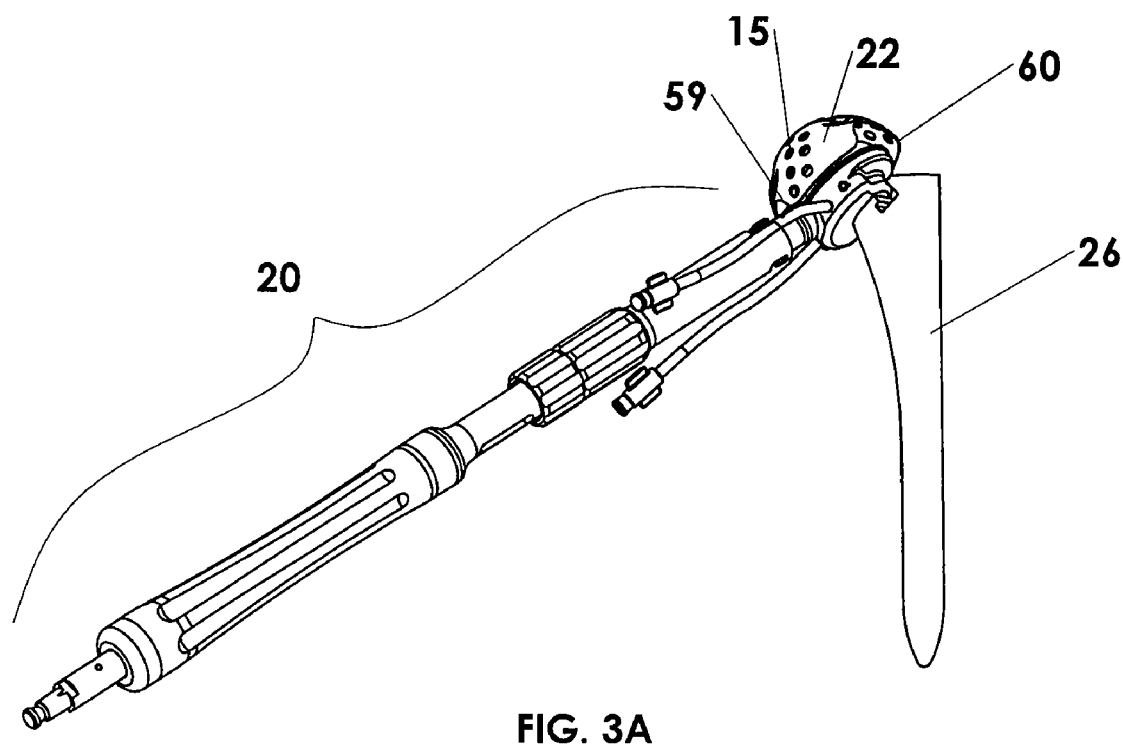
FIGS. 3A, 3B and 3C are perspective views of a reamer system in accordance with the present invention, including a handle, reamer drive, broach and grater, where the reamer system is depicted in collapsed, extended and exploded views, respectively.
Figure 3B:
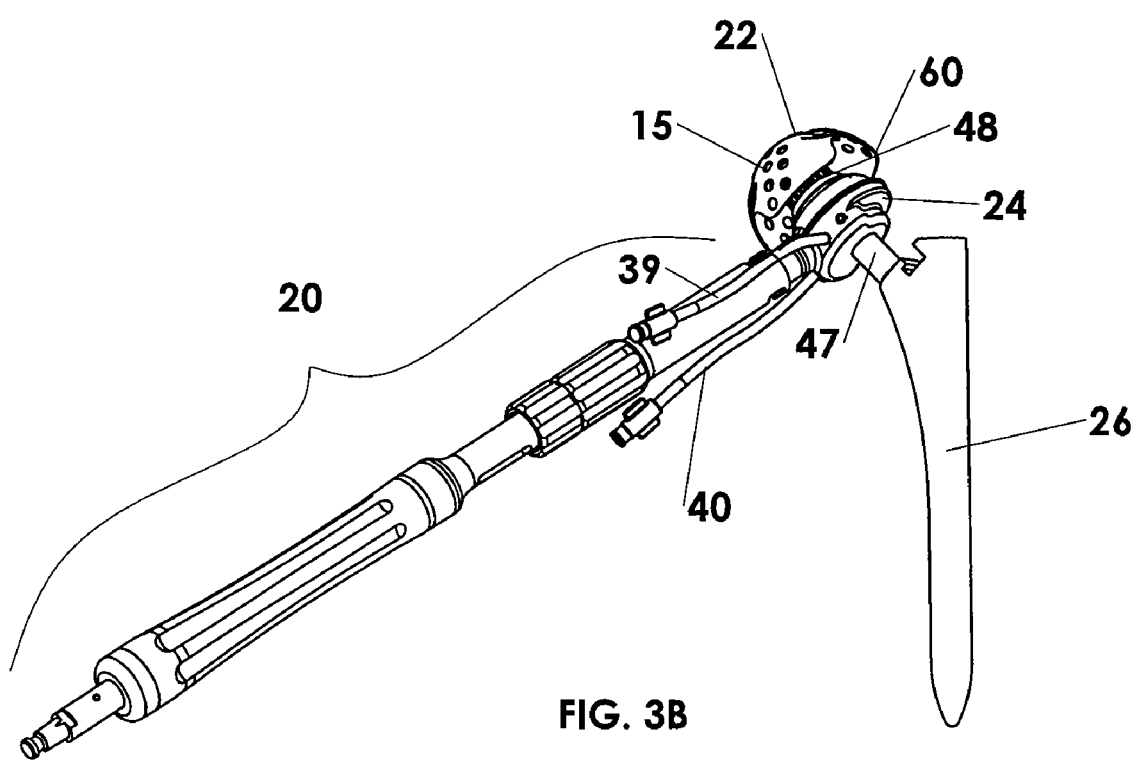
Figure 3C:
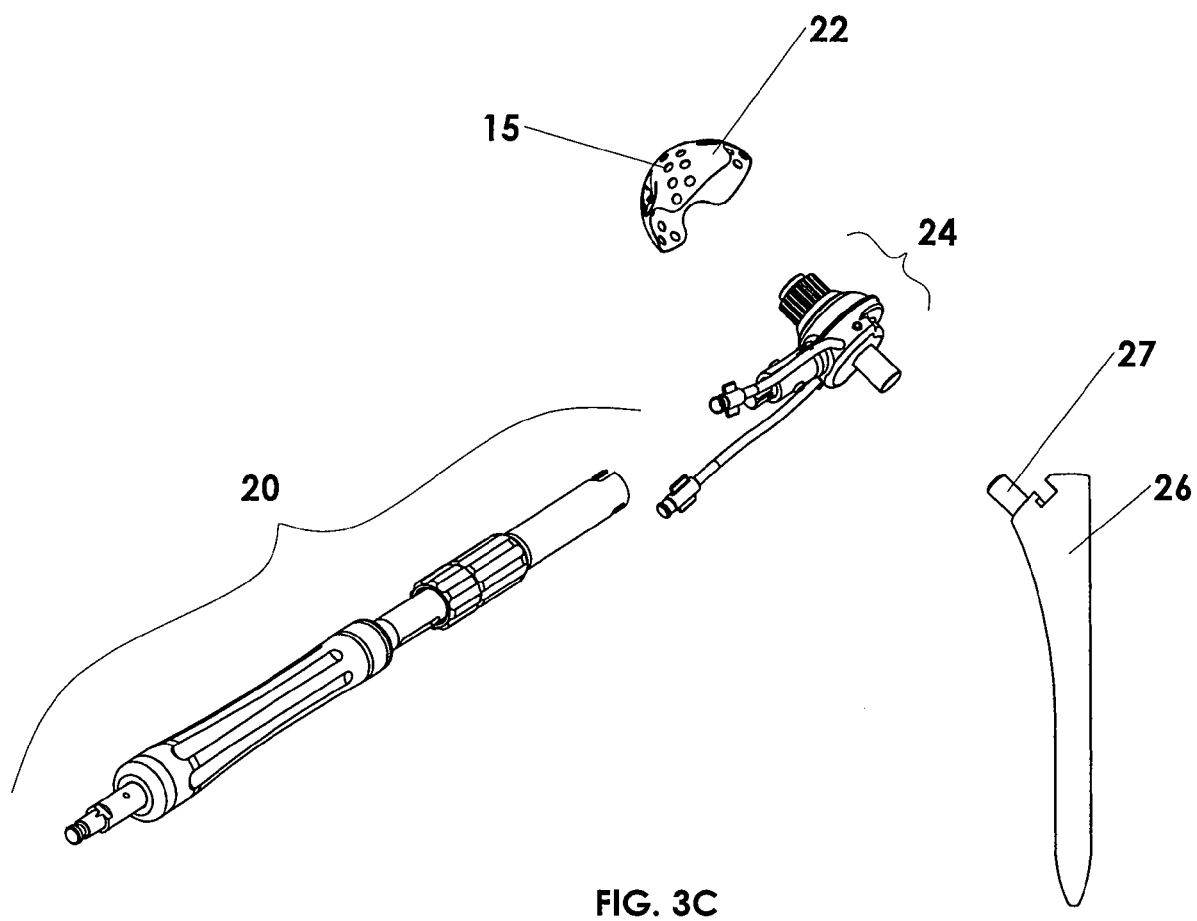
Figure 11A:
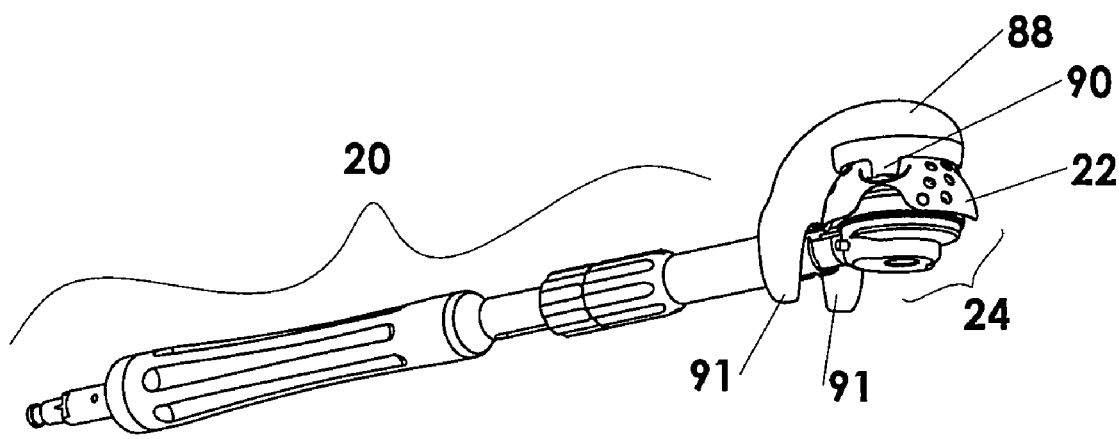
FIGS. 11A and 11B are perspective views of the reamer drive, handle, grater and grater removal tool in accordance with the present invention.
Figure 11B:
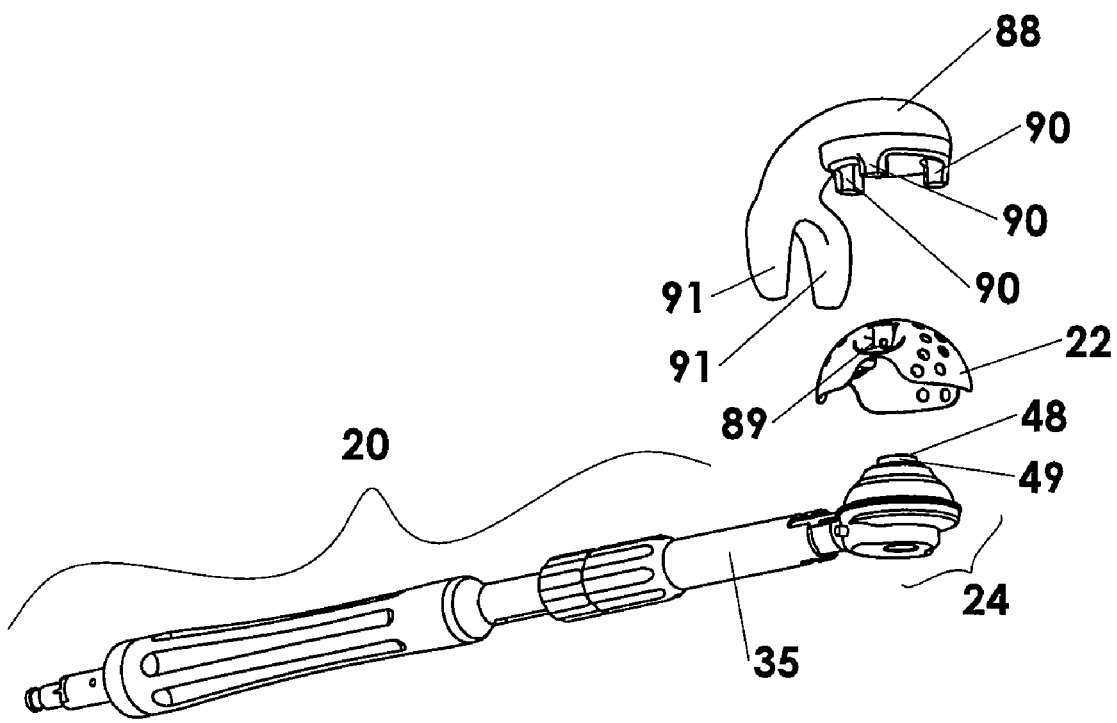
Figure 12A:
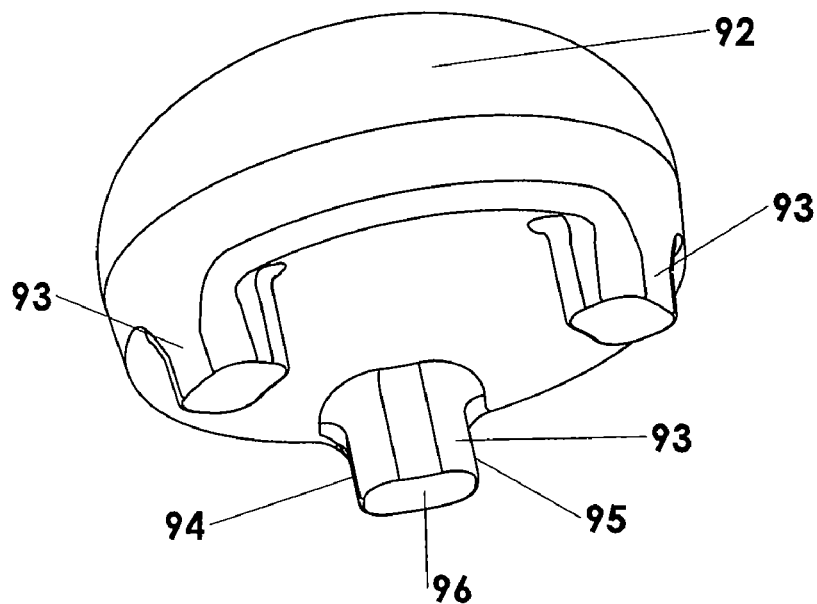
FIGS. 12A and 12B are perspective views of the reamer drive, handle, grater and grater release tool in accordance with the present invention.
Figure 12B:
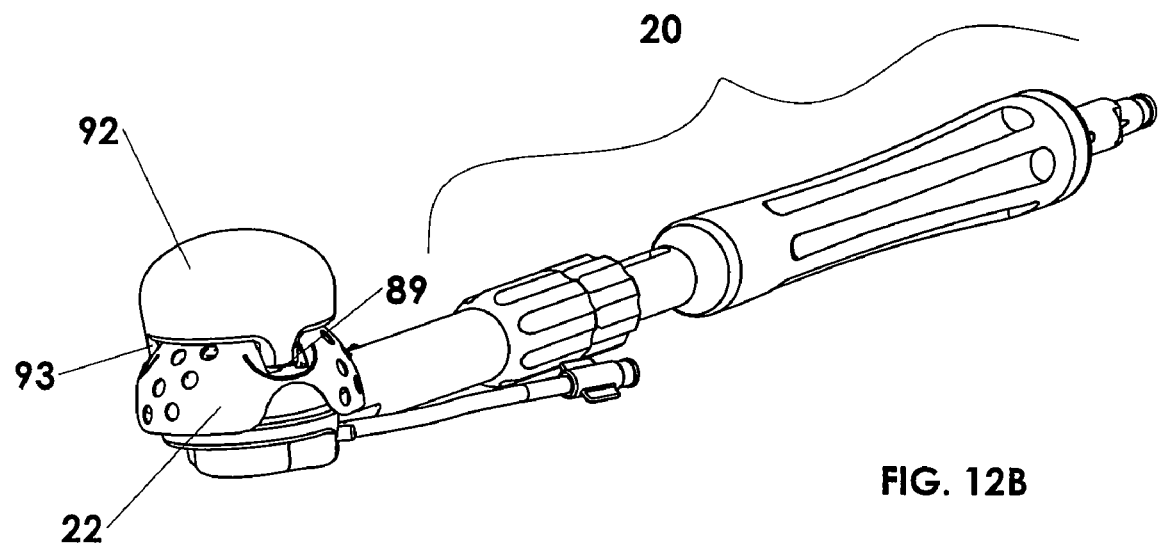

Referring again to FIG. 2, incision 21, muscle dissection and capsular incision are limited to what is necessary for adequate visualization, placement and operation of instrumentation and placement of implants. The general approach is posterior with no muscle release. Alternately, the surgeon may elect to release the piriformis tendon alone or in conjunction with partial or total release of the external rotators, quadratus femoris and gluteus minimus muscles. The incision is just large enough to expose the femoral head and acetabulum 12, and to enable placement of a reamer system including a grater 22, a reamer drive 24, a handle 20, and a femoral broach 26 as depicted in FIGS. 3A through 3C. A grater removal tool 88, as shown in FIGS. 11A and 11B, and a grater release tool 92, as shown in FIGS. 12A and 12B, can also be used with the reamer system. Optionally, one or more tissue distractors 18 may be used to hold soft tissue out of the line of sight or to distract tissue for instrument placement. Alternately, one or more of the tissue distractors may be integral to the handle 20, or may be integral to the reamer drive 24, or a combination thereof.

Reamer drive 24, handle 20, grater 22, femoral broach 26, grater removal tool 88, grater release tool 92, and/or structural sub-components of each of these are generally manufactured from a suitable stainless steel either by machining, metal injection molding or stamping. Alternately, materials, including but not limited to titanium and titanium alloys, cobalt chromium alloys, and other biocompatible metals, can be used. Biocompatible plastics such as PEEK, Ultem, Celcon, Delron and Radel may also be used for some sub-components. Sub-components fabricated from biocompatible plastics may be machined or injection molded.

Reamer drive 24, as shown in FIG. 3C, is used with handle 20, grater 22 and femoral broach 26 to prepare the acetabulum 12. Referring to FIGS. 3A and 3B, the femoral broach 26 is structured to prepare the proximal femur and remains in the femur to support the reamer drive 24. The reamer drive 24 is structured to extend once placed in the hip joint cavity. As shown in FIG. 3A, reamer drive 24 is collapsed to reduce the profile of reamer system for placement through a small incision. Reamer drive 24 is placed onto femoral broach 26 and hydraulically telescoped to distract femur 11 from acetabulum 12 while applying force to grater 22 in order to prepare acetabulum 12 to receive an implant. At least one passageway 59 is placed in a circumference of grater 22 to allow clearance of handle 20 when reamer drive 24 is fully retracted. Hydraulic pressure is applied to a spline tube 39 to extend a linear spline 48, which elevates grater 22 to allow a face 60 of grater 22 to pass over handle 20 while grater 22 rotates. Hydraulic pressure is applied to a piston tube 40 to extend a piston 47 that advances grater 22 into acetabulum 12 and provides a distraction force between femur 11 and acetabulum 12 to engage cutting elements 15 with material, such as cartilage and bone, of the acetabulum.

Figure 4A:
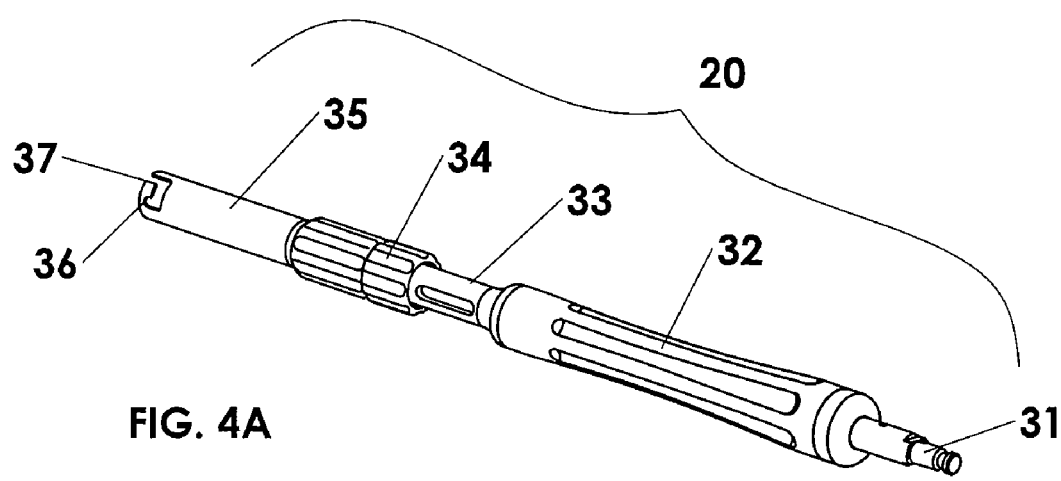
FIGS. 4A and 4B are perspective views of the handle in accordance with one embodiment of the present invention.
Figure 4B:
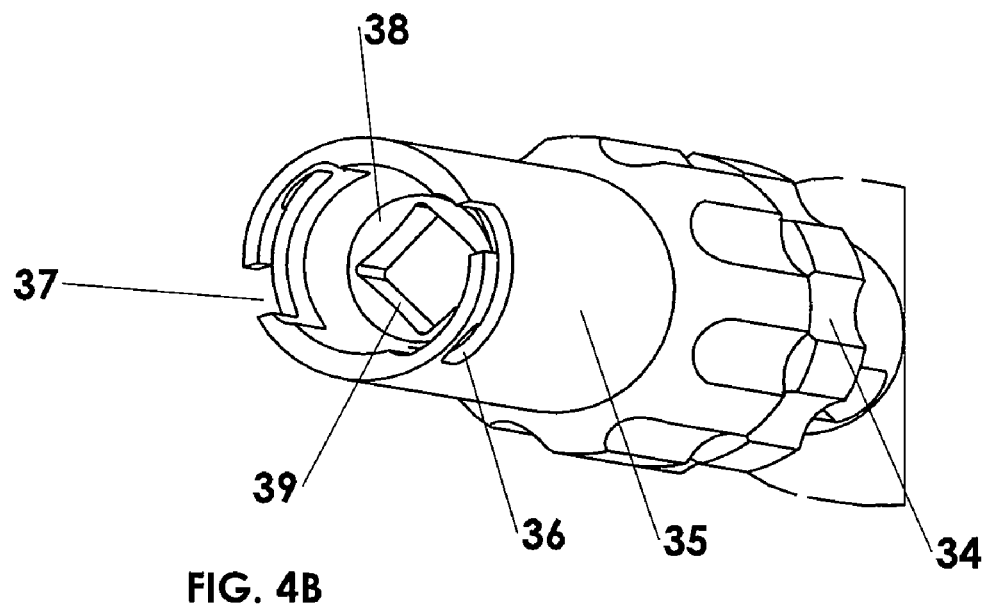
Figure 6A:
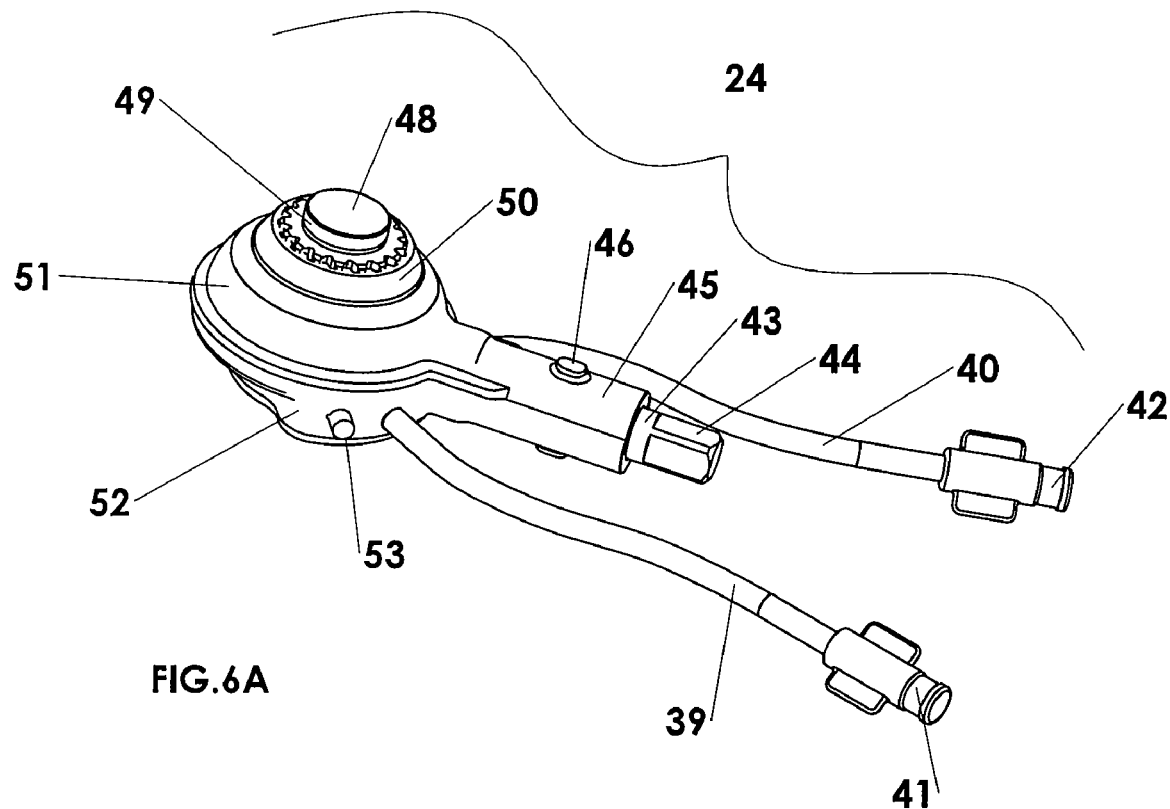
FIGS. 6A, 6B, 6C and 6D are top and bottom perspective views of the reamer drive in a collapsed position and an extended position, respectively, in accordance with an embodiment of the present invention.
Figure 6B:
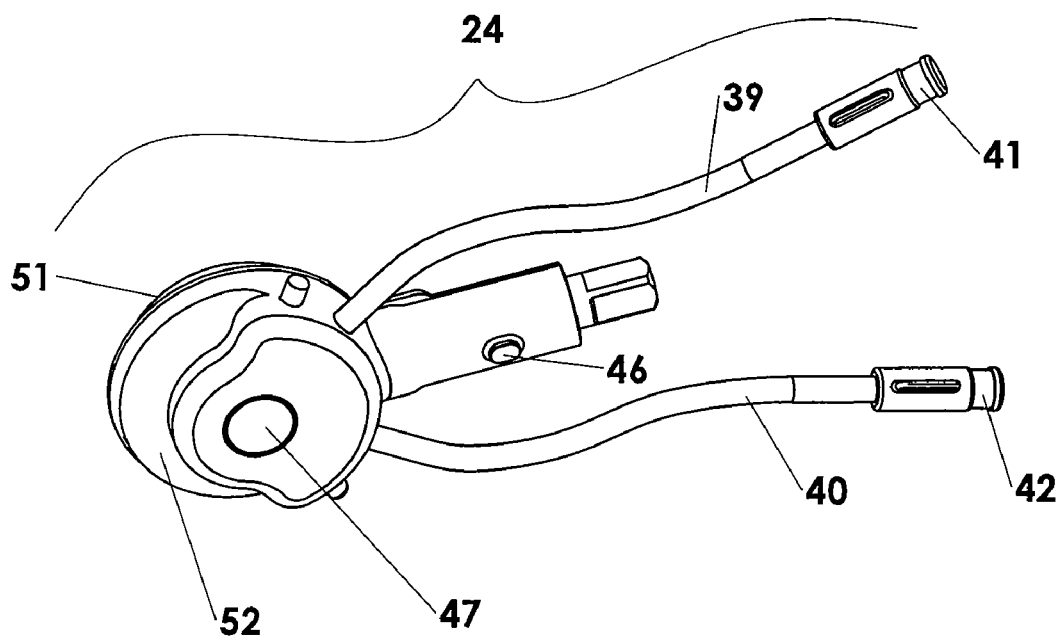
Figure 6C:
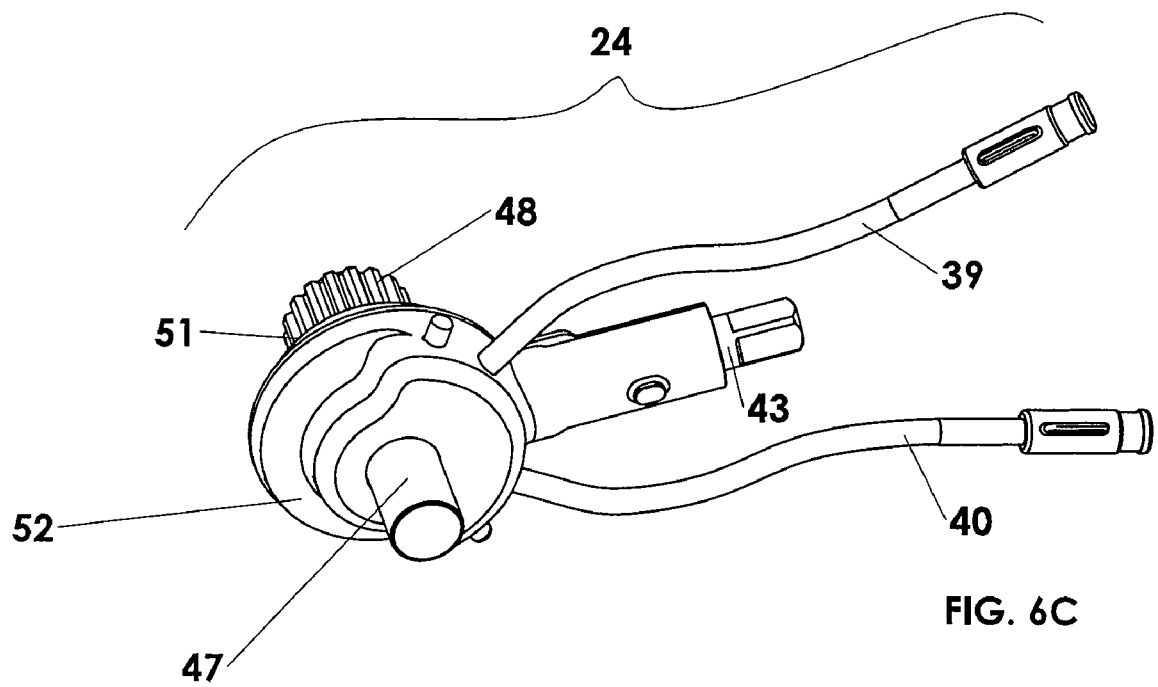
Figure 6D:
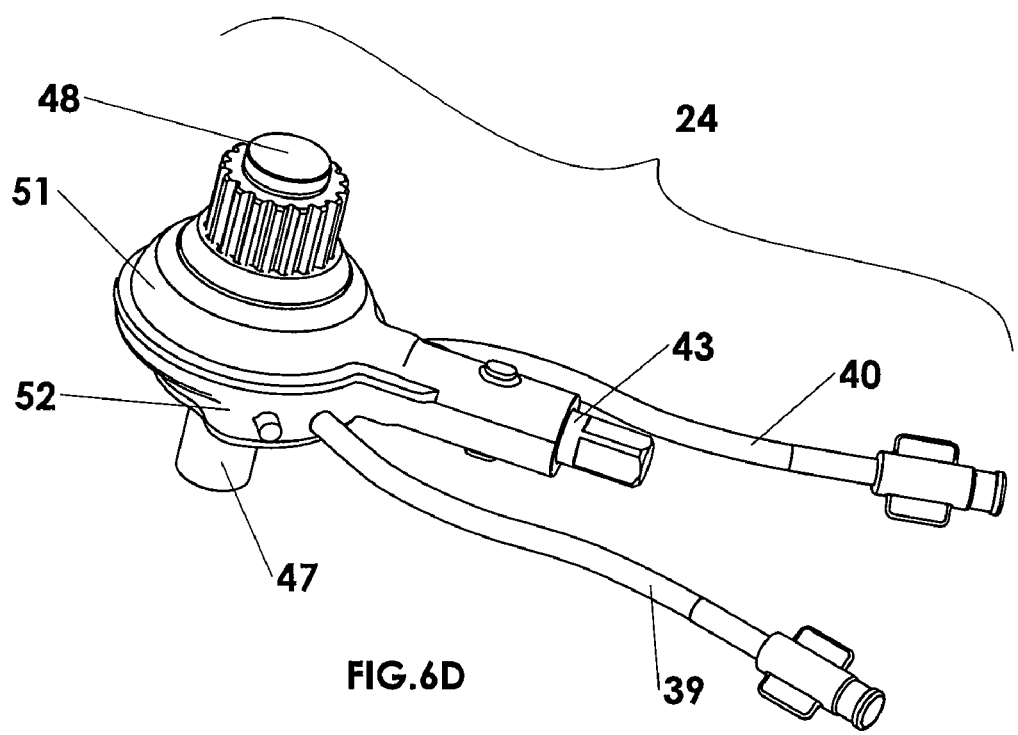

Referring now to FIGS. 4A and 4B, handle 20 is structured with an internal drive shaft 31 structured at one end with a Hudson fitting for attachment to a standard surgical drill. Alternately, the drive shaft 31 may be structured with a Hall adaptor, cylindrical, square, hexagonal or other shaped fitting suitable for attachment to a surgical drill can be used. A grip 32 is structured for easy handling by the surgeon and secured to a base 33 of handle 20. A barrel 35 is threaded onto base 33. A lock sleeve 34 is also threaded onto base 33 in order to secure barrel 35 to base 33. A barrel opening 37 is structured to slidably receive reamer drive 24, which engages a bayonet lock 36 in barrel 35. Referring to FIG. 6A, an attachment boss 45 on reamer drive 24 is structured to be slidably received into barrel opening 37. An external square drive 44 of a pinion gear 43, as shown in FIG. 6A, is structured to be slidably received into an internal square drive 29 of a drive shaft 38, as shown in FIG. 4B. Two bosses 46 protruding from attachment boss 45 of reamer drive 24 engage bayonet lock 36 in barrel 35 of handle 20. Barrel 35 extends along base 33 to provide clearance for attachment boss 45 to slide into barrel 35. Reamer drive 24 is rotated clockwise to engage bayonet lock 36 with bosses 46 protruding from attachment boss 45. Barrel 35 is threaded further onto base 33 thereby securing bosses 46 on attachment boss 45 of reamer drive 24 within bayonet lock 36. Lock sleeve 34 is then advanced to secure barrel 35 in place.

Referring to FIGS. 6A, 6B, 6C and 6D, reamer drive 24 is configured to extend in order to provide a distraction force between femur 11 and acetabulum 12 during acetabular reaming. Linear spline 48 is slidably received by a bevel gear 50 and housing base 52. Hydraulic pressure delivered to the cylinder housing the linear spline 48 by a fluid, such as sterile saline or other suitable liquid, via the spline tube 39 extends the linear spline 48. Spline tube 39 has a standard Luer fitting 41 for attachment to a syringe pump or other suitable pressurizing device. Piston 47 is configured to slidably receive a broach post 27 on femoral broach 26 as depicted in FIG. 3C. Hydraulic pressure, via a suitable fluid such as sterile saline, is applied to piston tube 40 to extend piston 47. Piston tube 40 has a standard Luer fitting 42 for attachment to a syringe pump or other suitable pressurizing device. In one embodiment as shown in FIGS. 3B and 6A, grater 22 is structured for threaded attachment to linear spline 48. In another embodiment, grater 22 is structured for quick attachment to reamer drive 24.

Figure 5:
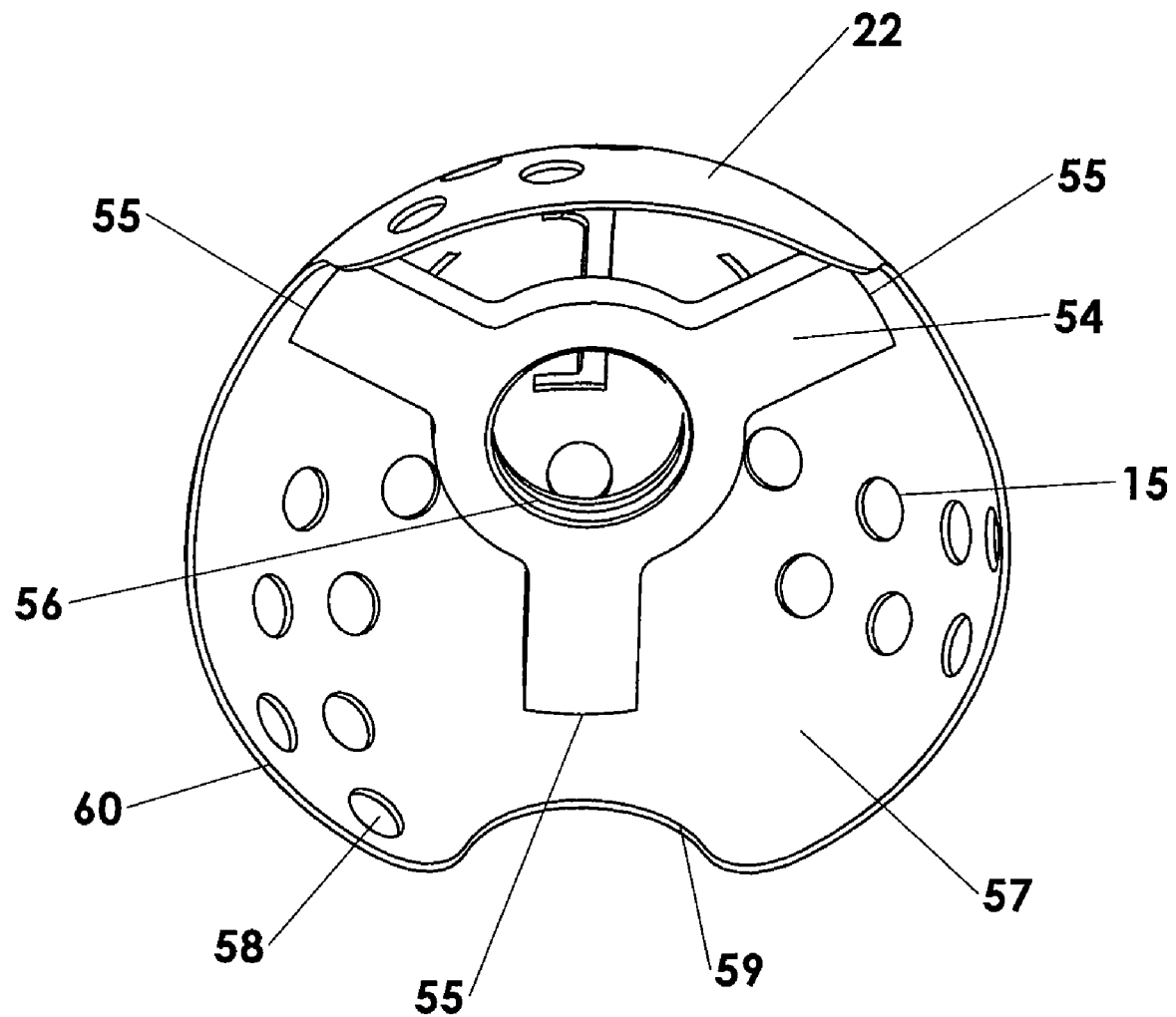
FIG. 5 is a bottom perspective view of the grater in accordance with one embodiment of the present invention.

Referring now to FIG. 5, grater 22 is structured for threaded attachment to reamer drive 24. A bracket 54 is secured to an inner surface 57 of grater 22 with bracket 54 at three attachment points 55. Those skilled in the art can appreciate that bracket 54 can be structured with one or more attachment points 55 to be attached to grater 22 as suitable for attachment around cutter openings 58. In one embodiment, bracket 54 is structured with an internal thread 56 for threaded attachment to linear spline 48 of reamer drive 24. Bracket 54 can be further attached to grater 22, for example via welding, soldering, and the like. A right hand thread is used at the bracket-to-linear-spline interface and the cutting action of grater 22 is in right hand rotation of grater 22. Operation of grater 22 to remove bone in accordance with this embodiment tends to tighten bracket 54 onto linear spline 48. Alternately, bracket 54 is structured to attach to grater 22 by a threaded attachment, bayonet attachment, press-fit attachment or bonded attachment, or with threaded fasteners, press-fit pins, mechanical clips, or other attachment means know to those skilled in the art.

In one embodiment, grater 22 is secured to linear spline 48 of reamer drive 24 such that linear spline 48 is removable from reamer drive 24. In this embodiment, linear spline 48 is structured to attach to grater 22 by a threaded attachment, bayonet attachment, press-fit attachment or bonded attachment, or with threaded fasteners, press-fit pins, mechanical clips, or other attachment means know to those skilled in the art. In another embodiment, linear spline 48 is permanently attached to grater 22 via welding, soldering, and the like.

Figure 7:
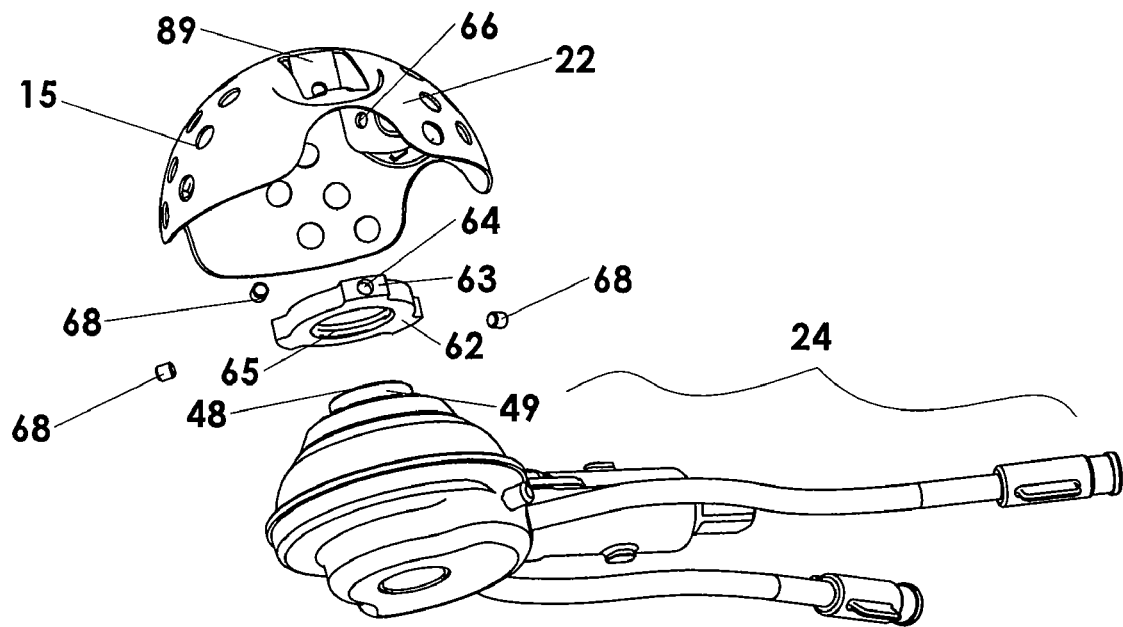
FIG. 7 is an exploded view of the grater threadably attached to the reamer drive in accordance with another embodiment of the present invention.

In one embodiment of the present invention, as shown in FIG. 7, grater 22 has formed tabs 61 to which a bracket 62 is attached. In this embodiment bracket 62 is structured with an internal thread 65 for threaded attachment to external thread 49 on linear spline 48 of reamer drive 24. Alternately, bracket 62 can be permanently attached to formed tabs 61 at contact points formed by one or more bosses 63 extending from bracket 62 to corresponding formed tabs 61. In another embodiment, the bracket-to-grater interfaces are secured with pins 68 placed through a clearance hole 66 in formed tabs 61 and fitted into a press-fit hole 64 in bracket bosses 63. Alternately, bracket 62 is structured to attach to grater 22 by a threaded attachment, bayonet attachment, press-fit attachment or bonded attachment, or with threaded fasteners, press-fit pins, mechanical clips, or other attachment means know to those skilled in the art.

Referring now to FIGS. 7 and 11A and 11B, grater 22 is removed by unthreading it from reamer drive 24 and/or linear spline 48. To simplify this step, a grater removal tool 88 is provided. Grater removal tool 88 has one or more protruding bosses 90 corresponding to each of a plurality of receiving pocket 89 in grater 22. Grater removal tool 88 is placed onto grater 22 with bosses 93 extending into respective receiving pockets 89 in grater 22. A reaction arm 91 on grater removal tool 88 rests against barrel 35 of handle 20 while the surgical drill (not shown) attached to handle 20 is run in reverse thereby unthreading grater 22 from reamer drive 24 and/or linear spline 48. Optionally, a T-handle driver (not shown) is used in place of the surgical drill to unthread grater 22 from reamer drive 24. Grater removal tool 88 and grater 22 are then lifted from reamer drive 24.

Figure 8:
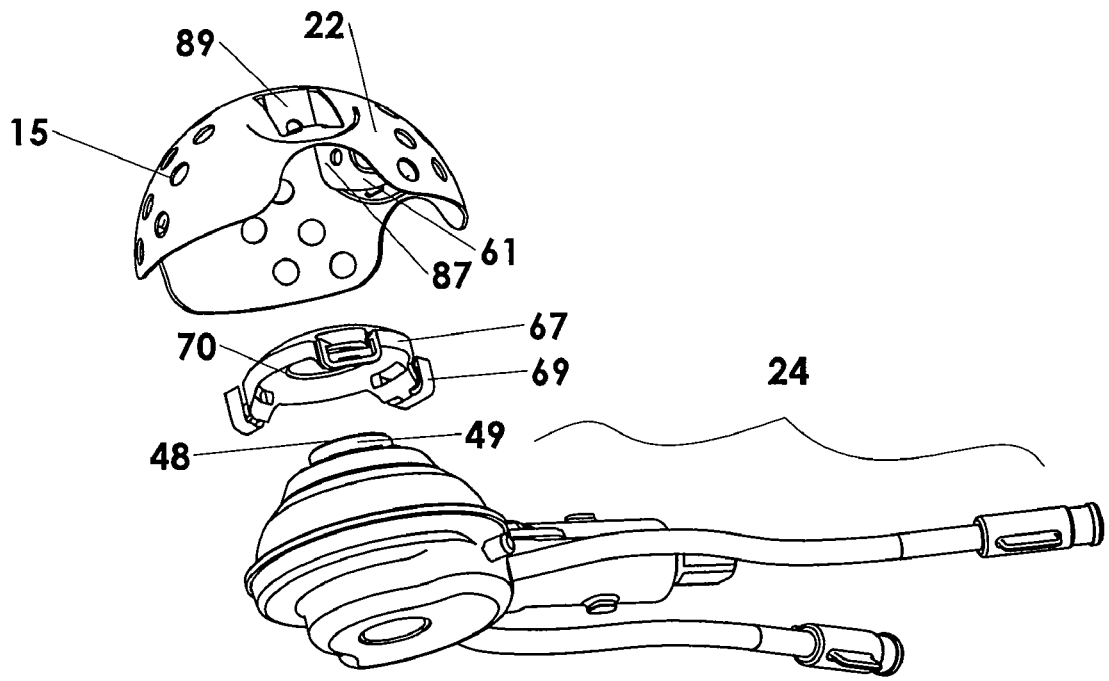
FIG. 8 is an exploded view of a quick attachment apparatus to connect the grater to the reamer drive in accordance with another embodiment of the present invention.
Figure 9:
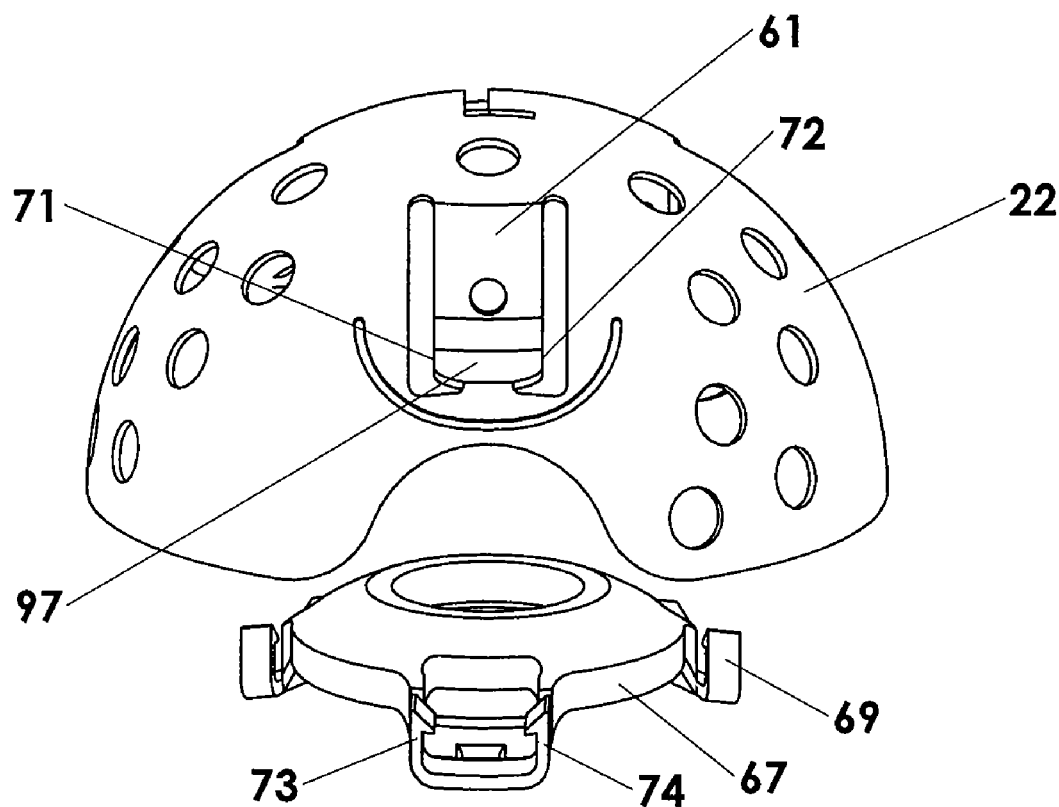
FIG. 9 is an exploded view of the grater and the attachment bracket shown in FIG. 8.
Figure 10:
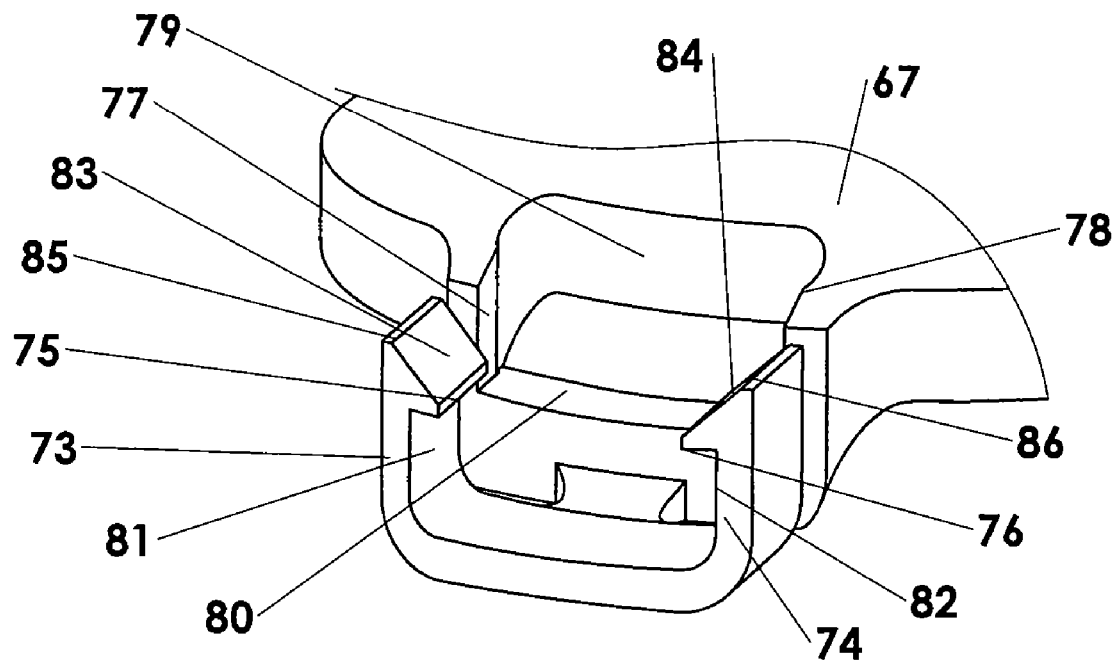
FIG. 10 is an enlarged perspective view of a portion of the attachment bracket shown in FIG. 9.

Referring now to FIG. 8 there is shown an embodiment of a bracket 67 including clips 69 for quick attachment to grater 22 in order to enable grater exchange without threading. Grater 22 has formed tabs 61 to which one or more clips 69 are attached. In this embodiment bracket 67 is structured with an internal thread 70 for threaded attachment to external thread 49 on linear spline 48 of reamer drive 24. Referring to FIGS. 8, 9 and 10, clip 69 is comprised of two flex arms 73 and 74 each having an internal latch 75 and 76, respectively. Internal surfaces 81 and 82 of clip 69 are spaced to snuggly receive formed tabs 61 resting on sides 71 and 72 of formed tab 61. Receiving surfaces 83 and 84 above internal latches 75 and 76 taper outwardly such that the spacing between upper edges 85 and 86 of each receiving surface 83 and 84, respectively, is greater than the spacing between sides 71 and 72 of formed tabs 61 when flex arms 73 and 74 are in their resting position. As grater 22 is pressed into clips 69 of bracket 67, formed tabs 61 slide along their respective receiving surfaces 83 and 84, thereby spreading flex arms 73 and 74 of clip 69. As formed tabs 61 pass over their respective internal latches 75 and 76 on bracket 67, internal latches 75 and 76 retain formed tabs 61 within clips 69 thereby locking grater 22 to bracket 67. When in the locked position, an inner face 87 of formed tabs 61 rests against a support face 79 of bracket 67 thereby centering grater 22 with respect to bracket 67. Sides 71 and 72 of formed tabs 61 are slidably received by internal support surfaces 77 and 78 of bracket 67 providing the ability to transfer torque from bracket 67 to grater 22. A right hand thread is used at the bracket-to-linear spline interface and the cutting action of grater 22 is in right hand rotation of grater 22. Operation of grater 22 to remove material, such as cartilage and bone, with cutting elements 15 on the hemispherical surface tends to tighten bracket 67 onto linear spline 48.

Referring to FIGS. 9, 10 and 12A and 12B, grater 22 is removed by releasing clips 69 of brackets 67 with the use of a grater release tool 92. Grater release tool 92 has one or more protruding bosses 93 each corresponding to clips 69 on bracket 67. Grater release tool 92 is placed onto grater 22 with bosses 93 extending into respective receiving pockets 89 in grater 22. A bottom surface 96 of each boss 93 comes to rest on an upper surface 97 of each formed tab 61 on grater 22. Boss sides 94 and 95 are slidably received by clip 69 receiving surfaces 83 and 84 thereby spreading flex arms 73 and 74 of clip 69 and releasing grater 22. Grater release tool 92 and grater 22 are then lifted from bracket 67.

In one embodiment of the present invention reamer drive 24, handle 20 and grater 22 are reusable components. Alternatively, handle 20 and grater 22 are reusable and reamer drive 24 is a single use or multiple use disposable device. In another embodiment, handle 20 is a reusable instrument and reamer drive 24 and grater 22 are single use or multiple use disposable devices. In yet another embodiment of the present invention grater 22 is integrally formed with reamer drive 24.

Now that each component of the present invention has been discussed, following is a discussion of a method of use of reamer system of the present invention. The hip joint cavity is exposed according to known techniques, including but not limited to those described above. The femoral canal is prepared using reamer drive 24 and femoral broach 26, where femoral broach 26 is left in the femoral canal. Reamer drive 24 and grater 22 are assembled and placed onto femoral broach 26. Those skilled in the art can appreciate that the sequence of instrument placement into the surgical site may vary based on surgeon preference and joint cavity access. Reamer drive 24 and grater 22 may be assembled outside the surgical site or within the joint cavity. Reamer drive 24 is assembled to handle 20 outside of the surgical site. An appropriately sized grater 22 is selected an attached to reamer drive 24. The surgeon selects grater 22, which is part of a set of graters of appropriate size range for preparing a patient's acetabulum. Grater 22 typically ranges from a diameter of 36 mm to 80 mm in one mm increments. In general, the surgeon will select an initial grater size smaller than the acetabular diameter for initial acetabular reaming.

In order to position grater 22 within acetabulum 12 in a minimally invasive manner, reamer drive 24 is initially collapsed as shown in FIG. 3A to reduce size for placement into the joint cavity. Once in position, reamer drive 24 is structured to expand as shown in FIG. 3C to provide a distraction force between the femur and acetabulum and grater 22 is positioned within acetabulum 12 in order to initiate the reaming process. The initial grater 22 is then exchanged for a larger grater, typically one mm larger in diameter, and the acetabular reaming step is repeated. This process is repeated until the acetabulum is appropriated prepare as determined by the surgeon to receive an implant. In order to allow interchangeability of grater 22 sizes with reamer drive 24, each grater 22 in the grater set is structured with a corresponding linear spline 48. In this manner, exchanging various size graters 22 is quick and efficient. To further simplify grater 22 exchanging during the reaming process, grater removal tool 88 and grater release tool 92 can be used to remove grater 22 from reamer drive 24 and/or linear spline 48. Upon completion of reaming process, acetabulum 12 is prepared for implantation of total hip replacement device according to techniques known in the art.

While the invention has been described with reference to the specific embodiments thereof, those skilled in the art will be able to make various modifications to the described embodiments of the invention without departing from the true spirit and scope of the invention. The terms and descriptions used herein are set forth by way of illustration only and are not meant as limitations. Those skilled in the art will recognize that these and other variations are possible within the spirit and scope of the invention as defined in the following claims and their equivalents.

What is claimed is:

1. A reamer system for preparing a joint for minimally invasive joint replacement comprising:
   i. a reamer drive having a top portion and a bottom portion including a reamer drive piston;
   ii. a grater having a first and a second surface, said first surface structured to remove material and said second surface structured to operably couple to the top portion of said reamer drive;
   iii. a handle having an internal drive shaft, said drive shaft having a first and a second end, said first end operably coupled to said reamer drive and said second end operably coupled to a power source; and
   iv. a femoral broach comprising a femoral attachment portion and a post attached to said femoral attachment portion, said post structured for engagably receiving said reamer drive piston.

2. The reamer system of claim 1 further comprising at least one tissue distractor coupled to said reamer drive.

3. The reamer system of claim 1 further comprising at least one tissue distractor coupled to said handle.

4. The reamer system of claim 1 wherein said reamer drive is operably coupled to a spline tube.

5. The reamer system of claim 1 wherein said second end of said handle is structured for attachment to a surgical drill.

6. The reamer system of claim 1 wherein said reamer drive is powered by an integral power source.

7. The reamer system of claim 6 wherein said power source is selected from the group consisting of electric, pneumatic, hydraulic, electromechanical or chemical.

8. The reamer system of claim 1 further comprising navigational tracker means operably coupled in part to said reamer drive.

9. The reamer system of claim 1 wherein said system is modular.

10. The reamer system of claim 1 wherein said system is non-modular.

11. The reamer system of claim 1 wherein said top portion of said reamer drive includes a bevel gear.

12. The reamer system of claim 11 wherein said bevel gear slidably receives a linear spline.

13. The reamer system of claim 12, said linear spline including a threaded circumference thereof for threadably receiving said grater.

14. The reamer system of claim 1 wherein said top portion of said reamer drive includes at least one clip for releasably receiving said grater.

15. The reamer system of claim 1 wherein said top portion further includes a bevel gear, said bevel gear slidably receiving said linear spline.

16. The reamer system of claim 13 wherein said grater includes an outer surface and an inner surface, said outer surface including cutter holes and said inner surface including a bracket operably attached to said grater at least one attachment point, said bracket including a threaded portion.

17. The reamer system of claim 16, said threaded portion of said bracket threadably receiving said threaded circumference of said linear spline.

18. A kit for preparing a joint for minimally invasive joint replacement comprising:
   a reamer system including
   i. a reamer drive having a top portion and a bottom portion including a reamer drive piston;
   ii. a grater set of multiple sizes, each of said graters having a first and second surface, said first surface structured to remove material and said second surface structured to operably couple to the top portion of said reamer drive;
   iii. a handle having an internal drive shaft, said drive shaft having a first and a seconds end, said first end operably coupled to said reamer drive and said second end operably coupled to a power source; and
   iv. a femoral broach comprising a femoral attachment portion and a post attached to said femoral attachment portion, said post structured for engagably receiving said reamer drive piston; and
   a grater removal tool capable of being operably coupled to said grater for removing said grater from said reamer drive.

19. A kit for preparing a joint for minimally invasive joint replacement comprising:
   a reamer system including
   i. a reamer drive having a top portion for receiving a grater and a bottom portion including a reamer drive piston;
   ii. a grater set of multiple sizes, each of said graters having a first and second surface, said first surface structured to remove material and said second surface structured to operably couple to said reamer drive;
   iii. a handle having an internal drive shaft, said drive shaft having a first and a second end, said first end operably coupled to said reamer drive and said second end operably coupled to a power source; and
   iv. a femoral broach comprising a femoral attachment portion and a post attached to said femoral attachment portion, said post structured for engagably receiving said reamer drive piston; and
   a grater release tool capable of being releasably coupled to said grater for releasing said grater from said reamer drive.

20. The reamer system of claim 1 further comprising a navigational tracker coupled at least in part to said handle.

21. A method for preparing a joint for minimally invasive joint replacement comprising:
   a. providing a reamer system, said system including a reamer drive having a top portion and a bottom portion including a reamer drive piston; a grater having a first surface and a second surface, said first surface structured to remove material and said second surface structured to operably couple to said reamer drive; a handle having an internal drive shaft, said drive shaft having a first and a second end, said first end operably coupled to said reamer drive and said second end operably coupled to a power source; a femoral broach comprising a femoral attachment portion and a post attached to said femoral attachment portion, said post structured for engagably receiving said reamer drive piston; and
   b. providing rotational motion generated by said power source, wherein said rotation motion is transferred through said drive shaft within said handle to said reamer drive and then to said grater.

22. The method of claim 21 further comprising providing hydraulic pressure to said reamer drive piston to extend and advance said grater towards an acetabulum from which said material is removed by said rotation motion of said grater.

23. A method for preparing a joint for minimally invasive joint replacement comprising:
   a. providing a reamer system, said system including a reamer drive having a top portion and a bottom portion including a reamer drive piston; a grater having a first surface and a second surface, said first surface structured to remove material and said second surface structured to releasably couple to the top portion of said reamer drive; a handle having an internal drive shaft, said drive shaft having a first and a second end, said first end operably coupled to said reamer drive and said second end operably coupled to a power source; a femoral broach comprising a femoral attachment portion and a post attached to said femoral attachment portion, said post structured for engagably receiving said reamer drive piston;
   b. placing said femoral broach into a femur; and
   c. providing rotational motion generated by said power source through said drive shaft within said handle to said reamer drive and then to said grater.

24. The method of claim 23 further comprising providing hydraulic pressure to said reamer drive piston to extend and advance said grater towards an acetabulum from which said material is removed by said rotation motion of said grater.

25. The method of claim 24 further wherein when appropriate material is removed with said grater, said grater being exchanged for a larger grater and steps b and c are repeated.

26. The method of claim 25 wherein said steps b and c are repeated until the acetabulum is prepared.

27. The method of claim 23 wherein said reamer drive and handle are operably coupled and said initial grater is releasably coupled to said reamer drive.

28. The method of claim 27 wherein said assembled handle, reamer drive and initial grater are place into the hip joint cavity.

29. The method of claim 23 wherein said reamer drive piston is engagably received by said broach post.

* * * * *